(12) United States Patent
Haslinger et al.

(10) Patent No.: US 8,487,275 B2
(45) Date of Patent: Jul. 16, 2013

(54) METHOD AND A DEVICE FOR MEASURING FLUORESCENCE LIFETIME

(75) Inventors: Robert Haslinger, Gröbenzell (DE); Patrick Leyendecker, Gräfeling (DE)

(73) Assignee: Deutsches Zentrum fur-Luft-und Raumfahrt E.V., Cologne (DE)

( * ) Notice: Subject to any disclaimer, the term of this patent is extended or adjusted under 35 U.S.C. 154(b) by 262 days.

(21) Appl. No.: 13/097,598

(22) Filed: Apr. 29, 2011

(65) Prior Publication Data

US 2011/0266461 A1    Nov. 3, 2011

(30) Foreign Application Priority Data

Apr. 30, 2010    (DE) .......................... 10 2010 019 095

(51) Int. Cl.
*G01J 1/58*    (2006.01)
(52) U.S. Cl.
USPC ..................... 250/459.1; 250/458.1; 356/317
(58) Field of Classification Search
USPC ................... 250/459.1, 458.1, 252.1
See application file for complete search history.

(56) References Cited

U.S. PATENT DOCUMENTS

| | | | | |
|---|---|---|---|---|
| 4,994,810 | A * | 2/1991 | Sinsky | 342/151 |
| 6,741,346 | B1 * | 5/2004 | Gerstner et al. | 356/318 |
| 2008/0024779 | A1 * | 1/2008 | Aasmul | 356/317 |
| 2008/0291808 | A1 * | 11/2008 | Hamaoka et al. | 369/112.02 |

FOREIGN PATENT DOCUMENTS

| | | |
|---|---|---|
| DE | 4344201 | 2/1997 |
| DE | 69402958 | 12/1997 |
| DE | 69320484 | 12/1998 |
| DE | 19829657 | 2/1999 |
| DE | 69505370 | 4/1999 |
| DE | 69326967 | 6/2000 |
| DE | 69328762 | 2/2001 |
| DE | 19951154 | 5/2001 |
| DE | 19956620 | 5/2001 |
| DE | 102005050151 | 11/2006 |
| DE | 102008012635 | 9/2009 |
| DE | 102008018475 | 10/2009 |
| WO | 9828592 | 7/1998 |

* cited by examiner

*Primary Examiner* — David Porta
*Assistant Examiner* — Abra Fein
(74) *Attorney, Agent, or Firm* — Ohlandt, Greeley, Ruggiero & Perle, LLP

(57) ABSTRACT

The invention refers to a method for measuring fluorescence lifetime. An excitation light radiation (12a), periodically modulated in a first frequency, is directed to a fluorescent material (20). For the measurement of fluorescence lifetime, the phase difference between the excitation light radiation (12a) and the fluorescent radiation (20a) is measured, the fluorescent radiation being detected by a fluorescent radiation detector (18).

According to the invention, a correction signal (16a), periodically modulated in a second frequency, is supplied to a measuring circuit (19), and a phase drift between the emitted correction signal (16a) and the correction signal (16a) processed by the measuring circuit is measured, the phase drift being caused by the measuring circuit. This phase drift is set off against the phase difference between the excitation light radiation (12a) and the fluorescent radiation (20a) which is measured by the fluorescent radiation detector (18), so as to compensate for the measuring error caused by the phase drift of the measuring circuit.

12 Claims, 1 Drawing Sheet

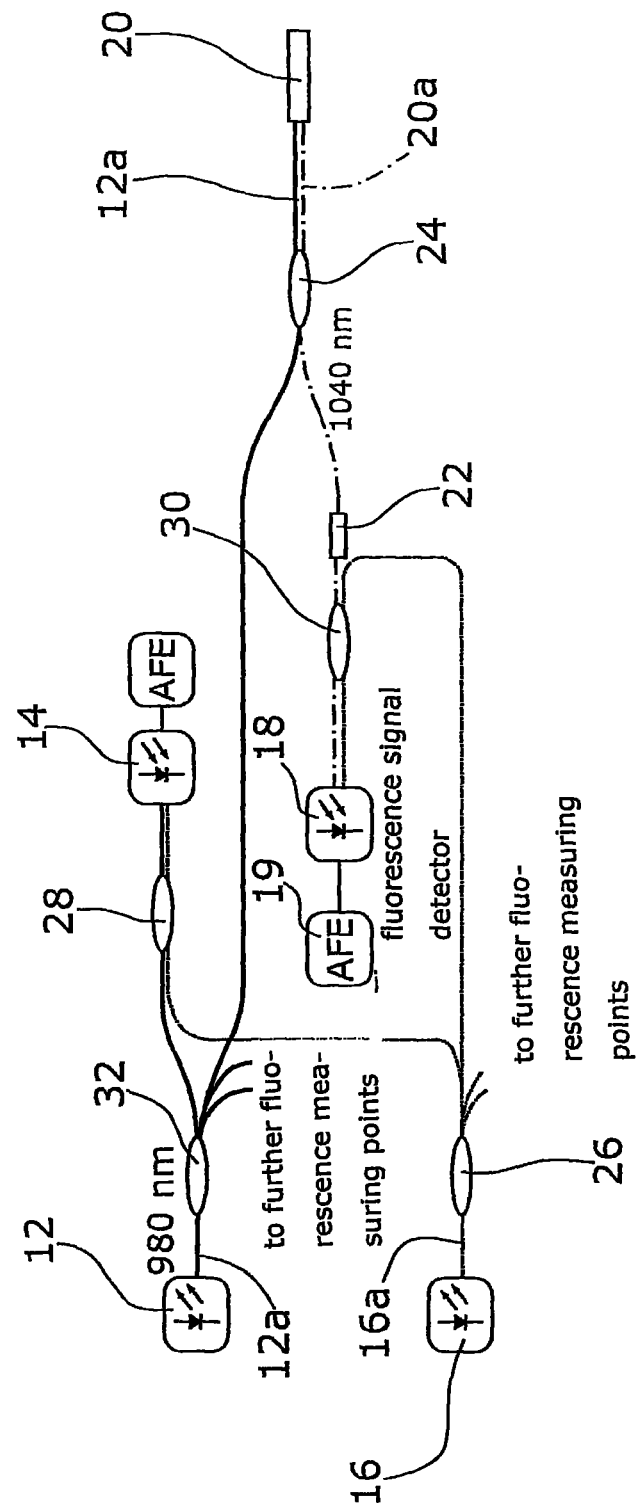

METHOD AND A DEVICE FOR MEASURING FLUORESCENCE LIFETIME

CROSS REFERENCE TO RELATED APPLICATIONS

The present invention claims the priority of German Patent Application no. DE 10 2010 019 095.0 filed on Apr. 30, 2010, the disclosures of which are incorporated herein by reference.

BACKGROUND OF THE INVENTION

1. Field of the Invention

The invention refers to a method as well as a device for measuring fluorescence lifetime.

2. Description of the Prior Art

The measurement of fluorescence lifetime is used in various applications. Depending on the material used, the lifetime of fluorescence is a function of external influences such as the pH value, the concentration of oxygen, expansion or temperature. For the purpose of measuring fluorescence lifetime, it is possible to measure the exponential decay of the fluorescence signal after a pulse-shaped excitation. As an alternative, it is possible to periodically excite (for example sinusoidally) the fluorescent medium or material, where the phase shift between the exciting radiation and the fluorescent radiation is measured. This phase shift is a direct measure of the fluorescence lifetime.

It is a problem with the latter measuring method that a phase drift caused by the evaluating electric circuit directly influences the signal to be measured. This drift may be caused, for instance, by external influences such as temperature, but also by the ageing of components. When the measured value changes, it is impossible to tell whether the effect is due to a change in the measured variable (namely the fluorescence lifetime) or to a phase drift in the system.

SUMMARY OF THE INVENTION

It is an object of the invention to provide a method and a device for measuring fluorescence lifetime that allow for a precise measurement.

In a method for measuring fluorescence lifetime an excitation light radiation, periodically modulated in a first frequency, is directed onto a fluorescent material. For the purpose of measuring fluorescence lifetime, the phase difference between the initial light radiation and the fluorescent radiation is measured, the fluorescent radiation being detected by a fluorescent radiation detector.

For a comparison between the phase position of the excitation light radiation and the fluorescent radiation received by the fluorescent radiation detector, it is possible to provide an excitation radiation reference detector that detects a part of the excitation light radiation.

According to the invention, a correction signal is supplied to a measuring circuit, which signal is periodically modulated in a second frequency. A phase drift, which is caused by the measuring circuit, between the outputted correction signal and the correction signal processed by the measuring circuit is measured. This phase drift is offset against, in particular subtracted from, the phase difference between the excitation light radiation and the fluorescent radiation measured by the fluorescent radiation detector. Thereby, the measurement error caused by the phase drift of the measuring circuit is compensated for.

The term "measuring circuit" is understood to refer to all electric or electronic components that can cause a phase drift. In particular, these may be the evaluating circuit, such as Analog Front Ends (AFE), for instance.

The correction signal may be coupled into the measuring system either electrically or optically. An electric coupling means that the correction signal is supplied directly to the measuring circuit. With an optical coupling, the correction signal may be a correction light radiation directed to the fluorescent radiation detector. Here, a phase drift is measured that the measuring circuit causes between the emitted correction light radiation and the correction light radiation detected via the fluorescent radiation detector. Thus, the fluorescent radiation detector converts the correction light radiation into an electric signal that is supplied to the measuring circuit as a correction signal.

For the purpose of measuring the phase difference between the excitation radiation and the fluorescent radiation, it is possible to alternatively use the control signal of the measuring light source by putting it in relation to the measured fluorescent radiation. It is preferred that the second frequency in which the correaction light radiation is modulated differs from the first frequency in which the excitation light radiation is modulated.

From the comparison between the emitted correction light radiation and the correction light radiation detected by the fluorescent radiation detector, a measured value for the phase drift is thus obtained, which phase drift is caused by interferences in the measuring system and can be cancelled arithmetically from the measuring signal. Thus, a correction signal is coupled into the optical path of the measuring system, whereby the interference effects can be measured independently of the frequency range and time-synchronously, so that phase drift effects can be eliminated.

It is preferred that, besides being periodically modulated in the second frequency, the correction light radiation is superposedly modulated in at least a further, third frequency that differs from the first and second frequencies. Thus, reference or measuring points for the compensation of interference effects can be determined at a plurality of positions in the spectrum.

It is particularly preferred that the second frequency is just below the first frequency and that the third frequency is just above the first frequency. This means that just above and just below the actual measuring frequency a correction signal is generated so that, for example, the drift of the analog filter in the measuring branch can be compensated for. The frequencies of the correction signal or the correction signals should preferably be chosen such that no interfering mixed products are formed that could corrupt evaluation. Firstly, it is preferred to avoid harmonic (multiple) frequencies when selecting the frequencies. Besides harmonic frequencies, image frequencies can occur in the sum frequency or the differential frequency of the respective signals. The frequency of the correction signal is therefore preferably chosen such that mixed frequencies in the frequency range of the actual measuring frequency will only occur for higher order mixtures.

The invention further refers to a device for measuring fluorescence lifetime. The device comprises a measuring light source for emitting an excitation light radiation, periodically modulated in a first frequency, towards a fluorescent material. The device further comprises a fluorescent radiation detector for measuring a fluorescent radiation emitted by the fluorescent material due to the excitation thereof by the excitation light radiation.

According to the invention, a correction signal source is provided for supplying a correction signal, periodically modulated in a second frequency, to a measuring circuit. Here, a phase drift between the correction signal supplied and the measuring signal processed by the measuring circuit is measured, which phase drift is caused by the measuring circuit. This phase drift is set off against, in particular subtracted from the phase difference between the excitation light radiation and the fluorescent radiation measured by the fluorescent radiation detector, whereby the measuring error caused by the phase drift of the measuring circuit is compensated for.

As already described in the context of the method according to the invention, it is possible to couple in the correction signal either electrically or optically. With an optical coupling the correction signal source is in the form of a correction light source emitting correction light radiation to the fluorescent radiation detector. Here, the phase drift between the emitted correction light radiation and the correction light radiation detected by the fluorescent radiation detector is measured, which phase drift is caused by the measuring circuit.

In a preferred embodiment, the device comprises an excitation radiation reference detector for detecting a part of the excitation radiation to be used in a comparison of the phase position of the excitation radiation with the fluorescent radiation received by the fluorescent radiation detector, so as to determine thereby the resulting phase difference. As already explained, it is a possible alternative to use the control signal of the excitation radiation instead of the excitation radiation reference detector.

Moreover, the device may include a correction radiation blocker arranged between the fluorescent radiation detector and the fluorescent material. The same serves to block possible reflections of the correction light radiation towards the fluorescent material. In particular, the correction radiation blocker may be an optical isolator, a fiber Bragg grating, a wavelength-selective coupler, an optical circulator or a combination of a plurality of these components.

Preferably, the measuring light source and/or the correction light source are configured as a laser diode, a superluminescence diode (SLD), a luminous diode (LED), an edge-emitting LED (EE-LED) or an ASE light source.

The components of the device may be coupled with each other via optical wave guides. Moreover, some or all components of the device may be realized as free space components. Further, the components of the device may be designed entirely or in part as an integrated optical circuit and in particular as a planar waveguide structure.

All features described in the context of the present device are applicable to the present method and vice versa.

BRIEF DESCRIPTION OF THE DRAWINGS

A full and enabling disclosure of the present invention including the best mode thereof, enabling one of ordinary skill in the art to carry out the invention, is set forth in greater detail in the following description, including reference to the accompanying drawing in which the sole FIGURE illustrates the schematic structure of an embodiment of the present invention.

DESCRIPTION OF PREFERRED EMBODIMENTS

In the system illustrated, the fluorescence lifetime of ytterbium atoms (Yb) is measured in a length of doped single mode fiber (SM fiber) 20. The ytterbium is illuminated by means of a laser diode 12 (wavelength of 980 nanometers) which is modulated sinusoidally. A part of the excitation signal or the excitation light radiation 12a is directed to the excitation radiation reference detector 14. In the present case, the emission spectrum of the fiber 20 excited to fluorescent radiation is in the range of 1040 nanometers. Thus, it can be separated from the excitation radiation 12a using a wavelength division multiplexer (WDM) 24.

The correction light source 16 is sinusoidally modulated at another frequency than the measuring frequency (i.e. the first frequency with which the excitation radiation is modulated). In the case illustrated, the correction light source 16 also emits light at a wavelength of 980 nanometers.

The correction light radiation 16a is split by a splitter 26 and directed to the excitation radiation reference detector 14 by means of a coupler 28, as well as to the fluorescent radiation detector 18 by means of another wavelength division multiplexer or coupler 30. For the purpose of preventing possible reflections of the correction light radiation 16a into the fluorescent material 20, a correction radiation blocker 22 may be provided.

The other outputs of the splitters 26 and 32 may lead to further measuring points, wherein these only require the fluorescent radiation detector path (including the fluorescent medium 20), respectively. The excitation radiation reference detector 14 may be used in common for all measuring points, as can the light sources. By means of the method illustrated interfering drift effects caused by the electronics (the analog front ends (AFE) in the FIGURE) can be compensated for.

A non-illustrated depolarizer may optionally be provided behind the light sources so as to minimize polarization-dependent effects.

Depending on the wavelengths used, the coupler may in part be WDMs. Conversely, WDMs may be designed in part as couplers. The WDM 24 upstream of the measuring point may also be replaced with an optical circulator.

The method of the invention, as well as the device of the invention is applicable in all fields in which fluorescent lifetime measurements are made. Exemplary applications are measurements of temperature, pH value or oxygen concentration. Possible fields of application are the domain of laboratories, industrial production or medical technology.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

The invention claimed is:

1. A method for measuring fluorescence lifetime, wherein an excitation light radiation, periodically modulated in a first frequency, is directed to a fluorescent material, and for the measurement of fluorescence lifetime, the phase difference between the excitation light radiation and the fluorescent radiation is measured, the fluorescent radiation being detected by a fluorescent radiation detector, wherein a correction signal, periodically modulated in a second frequency, is supplied to a measuring circuit, and that a phase drift between the emitted correction signal and the correction signal processed by the measuring circuit is measured, the phase drift being caused by the measuring circuit, wherein this phase drift is set off against the phase difference between the excitation light radiation and the fluorescent radiation which is measured by the fluorescent radiation detector, so as to compensate for the measuring error caused by the phase drift of the measuring circuit.

2. The method for measuring fluorescence lifetime as defined in claim 1,
wherein
a correction light radiation, periodically modulated in a second frequency, is directed to the fluorescent radiation detector as the correction signal, and wherein a phase drift between the emitted correction light radiation and the correction light radiation detected by the fluorescent radiation detector is measured, the phase drift being caused by the measuring circuit.

3. The method for measuring fluorescence lifetime as defined in claim 2, wherein, besides the periodical modulation in said second frequency, the correction light radiation is superposedly modulated in at least a further frequency that differs from the first and second frequencies.

4. The method for measuring fluorescence lifetime as defined in claim 3, wherein the second frequency is just below the first frequency and the third frequency is just above the first frequency.

5. A device for measuring fluorescence lifetime comprising
a measuring light source for emitting an excitation light radiation, periodically modulated in a first frequency, towards a fluorescent material,
a fluorescent radiation detector for the measurement of fluorescent radiation emitted by the fluorescent material due to the excitation by said excitation light radiation,
characterized by
a correction signal source for supplying a correction signal, periodically modulated in a second frequency, to a measuring circuit, wherein a phase drift between the emitted correction signal and the correction signal processed by the measuring circuit is measured, the phase drift being caused by the measuring circuit,
wherein this phase drift is set off against the phase difference between the excitation light radiation and the fluorescent radiation which is measured by the fluorescent radiation detector, so as to compensate for the measuring error caused by the phase drift of the measuring circuit.

6. The device for measuring fluorescence lifetime as defined in claim 5,
characterized by
a correction light source as a correction signal source for emitting correction light radiation, periodically modulated in a second frequency, to the fluorescent radiation detector, and wherein a phase drift between the emitted correction light radiation and the correction light radiation detected by the fluorescent radiation detector is measured, the phase drift being caused by the measuring circuit.

7. The device for measuring fluorescence lifetime as defined in claim 6, comprising an excitation radiation reference detector for detecting a part of the excitation radiation for a comparison between the phase position of the excitation radiation and the fluorescent radiation received by the fluorescent radiation detector, so as to determine the phase difference resulting therefrom.

8. The device for measuring fluorescence lifetime as defined in claim 6, comprising a correction radiation blocker arranged between the fluorescent radiation detector and the fluorescent material to block any reflection of said correction light radiation in the direction of the fluorescent material, wherein said correction radiation blocker may be, in particular, an optical isolator, a fiber Bragg grating, a wavelength-selective coupler, an optical circulator or a combination of a plurality of these components.

9. The device for measuring fluorescence lifetime as defined in claim 6, wherein the measuring light source and/or the correction light source are configured as a laser diode, a super-luminescence diode (SLD), a luminous diode (LED), an edge-emitting LED (EE-LED) or an ASE light source.

10. The device for measuring fluorescence lifetime as defined in claim 6, wherein the components of the device are coupled with each other by means of optical waveguides.

11. The device for measuring fluorescence lifetime as defined in claim 6, wherein some or all components of the device are realized as free space components.

12. The device for measuring fluorescence lifetime as defined in claim 6, wherein the components of the device may be designed entirely or in part as an integrated optical circuit and in particular as a planar waveguide structure.

* * * * *